United States Patent

Clausen et al.

[11] Patent Number: 5,879,669
[45] Date of Patent: Mar. 9, 1999

[54] AQUEOUS HAIR FIXING COMPOSITION CONTAINING A WATER-SOLUBLE HAIR FIXING POLYMER AND A THICKENER

[75] Inventors: Thomas Clausen, Alsbach; Günther Lang, Reinheim; Wolfgang Keil, Mühlheim; Michael Franzke, Rossdorf; Jürgen Schmenger, Weiterstadt; Dieter Schonert, Reinheim, all of Germany

[73] Assignee: Wella Aktiengesellschaft, Darmstadt, Germany

[21] Appl. No.: 664,115

[22] Filed: Jun. 14, 1996

Related U.S. Application Data

[63] Continuation-in-part of Ser. No. 351,369, Dec. 8, 1994, abandoned.

[51] Int. Cl.$^6$ ....................................................... A61K 7/06
[52] U.S. Cl. ..................................... 424/70.11; 424/70.13; 424/70.15; 424/70.16; 424/70.17; 424/70.21; 424/70.22; 424/70.31; 524/55
[58] Field of Search ............................... 424/70.11, 70.13, 424/70.15, 70.16, 70.17, 70.21, 70.22, 70.31; 524/55

[56] References Cited

U.S. PATENT DOCUMENTS 4,591,610  5/1986  Grollier ...................................... 524/55
4,886,660  12/1989  Patel et al. ................................ 424/70

FOREIGN PATENT DOCUMENTS 2222949  3/1990  United Kingdom .

*Primary Examiner*—Randy Gulakowski
*Attorney, Agent, or Firm*—Michael J. Striker

[57] ABSTRACT

The aqueous hair fixing composition contains 0.1 to 30 percent by weight of at least one thickener, e.g. acrylic acid polymer; 0.1 to 25 percent by weight of a film-forming polymer ingredient which consists of vinyl acetate/crotonic acid copolymer, acrylic acid/acrylamide copolymer and/or methyl vinyl ether/maleic anhydride copolymer and 45 to 99.8 percent by weight water. This aqueous hair fixing composition necessarily contains no organic solvents, no cationic surfactants and no cationic polymers and a physiologically acceptable acid or base is added to it to adjust its pH so that the film-forming polymer ingredient is at least partially precipitated.

10 Claims, No Drawings

AQUEOUS HAIR FIXING COMPOSITION CONTAINING A WATER-SOLUBLE HAIR FIXING POLYMER AND A THICKENER

This is a continuation-in-part of U.S. patent application Ser. No. 08/351,369, filed Dec. 8, 1994, and now abandoned.

BACKGROUND OF THE INVENTION

The invention relates to an aqueous composition for treating hair, especially to a hair fixing composition, which contains a thickener and a fixing or film-forming polymer which can be precipitated completely or partially in aqueous solution by changing the pH value, has a pH value at which it is precipitated completely or partially and is soluble at other pH values.

Conventional hair treatment compositions containing natural, synthetic or modified natural film-forming polymers generally take the form of alcoholic preparations, aqueous-alcoholic preparations or preparations containing some other organic solvent.

When used daily, organic solvents in hair grooming products have a negative effect on humans and on the environment. They also have an unpleasant odor. If the organic solvent contained in such compositions is replaced by water, this usually leads to a deterioration of its useful properties, e.g., results in slow drying of hair. In such cases, the hair usually feels sticky.

Hair fixing compositions with an intensive setting or fixing action contain high proportions of one or more film-forming fixing polymers so that the use of such compositions greatly burdens the hair, particularly fine hair. Moreover, hair can become sticky.

Currently conventional forms for such compositions are sprays, lotions, foams and gels. The problems mentioned above frequently occur with gels in particular.

Further, hair treatment compositions in gel form have limited fixing or holding power.

European Patent Application EP-OS 0 445 714 describes hair fixing compositions containing sodium alginate, a fixing polymer and water as solvent. However, the fixing power of such compositions is limited. Furthermore, they can burden hair.

European Patent Application EP-OS 0 412 705 discloses a cosmetic hair composition which contains a nonionic, water-soluble thickening polymer which is modified with respect to hydrophobic properties, a second water-soluble thickening polymer and a hair-fixing polymer which is soluble or insoluble in water. Special silicone copolymers which are dissolved in liquid silicone derivatives are worked into the composition as preferred fixing polymers. Due to the use of silicon-organic solvents, such compositions are not sufficiently environmentally friendly.

A hair care composition with holding properties containing a water-insoluble polymeric complex is described in European Patent Application EP 0 034 190 A1. The insoluble polymeric complex is a reaction product of an anionic polymer and a cationic surfactant. This reaction product imparts body and stiffness to the hair (page 1, lines 20 to 32). However, the hair fixing power of such compositions is limited and the requirement of the complex forming cationic surfactant substantially increases the production costs.

SUMMARY OF THE INVENTION

Therefore, the object of the present invention is to provide a composition for treating hair, especially a hair fixing composition, which does not have the disadvantages mentioned above.

Surprisingly, it has now been found that this object is attained in an outstanding manner by a composition for treating hair which contains (A) 0.1 to 30 percent by weight of at least one organic and/or inorganic thickener;

(B) 0.1 to 25 percent by weight of at least one film-forming polymer which can be precipitated completely or partially by changing the pH, and (C) 45 to 99.8 percent by weight water, which (D) contains no organic solvents, no cationic polymers and no cationic surfactants, and (E) has a pH at which component (B) is completely or partially precipitated.

The hair treatment composition preferably contains 0.15 to 15 percent by weight of component (A). The thickeners of component (A) may be selected from the class of natural, modified-natural and/or synthetic thickeners. Examples of preferred synthetic thickeners include polymers and copolymers of acrylic acid, polymers and copolymers of methacrylic acid, polymers and copolymers of crotonic acid or polymers and copolymers of salts or esters of acrylic acid, methacrylic acid or crotonic acid, e.g., polyacrylic acid (CTFA adopted name: Carbomer) as sold by B. F. Goodrich (U.S.A.) under the tradename Carbopole® or by Sigma (Italy) under the trade name Acrisint®, copolymers formed from acrylamide and sodium acrylate (CTFA: Acrylamide/Sodium Acrylate Copolymer), e.g., Hostacerin PN 73® of Hoechst (Germany), copolymers formed from a stearyl alcohol methacrylic acid ester ethoxylated with 20 moles ethylene oxide and acrylic acid (CTFA: Acrylates/Steareth-20 Methacrylate Copolymer), e.g., Acrysol ICS-1® of Rohm and Haas (U.S.A.), and copolymers of unsaturated acid anhydrides and alkyl vinyl ethers crosslinked with dienes or PVM/MA copolymers, e.g., a copolymer of methyl vinyl ether and maleic anhydride crosslinked with decadiene, Stabileze® 06 of ISP (U.S.A.).

Further, polyethylene glycols, polypropylene glycols or polyethylene glycol/polypropylene glycol copolymers can be used as synthetic thickeners.

The names of the polymers mentioned by way of example were taken from the CTFA Cosmetic Ingredient Dictionary, 4th edition, 1991.

Preferred natural or modified-natural thickeners are, e.g., polysaccharides, their derivatives or hydrolyzates. Examples of such compounds are cellulose and cellulose derivatives, starch and starch derivatives, chitin and chitin derivatives, chitosan and chitosan derivatives, alginic acid and alginates, carrageenan, malto-dextrin, dextrin, guar gum, xanthan gum, gellan gum, and hyaluronic acid and salts of hyaluronic acid. Also, gelatin, hectorite or bentonite can be used as thickeners.

The hair treatment composition preferably contains 0.2 to 10 percent by weight of the film-forming polymers of component (B). For example, film-forming natural, modified-natural or synthetic polymers formed from monomers with acidic, alkaline or acidic and alkaline functional groups can be used as compounds of component (B).

These functional groups include carboxyl groups, hydroxyl groups, sulfonic groups or phosphate groups, their salts, free or substituted amino groups or their salts, etc. The composition according to the invention preferably contains film-forming or fixing polymers which are soluble in water in their salt form, but insoluble in water as free base and/or acid. If both acidic and alkaline groups are contained in the polymer (amphoteric polymers), this polymer is soluble in the acidic range as well as in the alkaline range so that the polymer can only be precipitated at tile isoelectric point. The isoelectric point for such polymers is preferably in the pH range of 3 to 8.5. The synthetic copolymers, graft copolymers or terpolymers used in the composition according to the invention preferably contain, as monomer building blocks, compounds from the group of unsaturated monocarboxylic and dicarboxylic acids or anhydrides of dicarboxylic acids, e.g., methacrylic acid, maleic acid, maleic acid anhydride or crotonic acid. The polymer contains unsaturated organic compounds, preferably unsaturated carboxylic acids and/or their derivatives, vinyl esters and/or their saponification products, vinyl amines, vinyl amides, vinyl ethers, vinyl lactones, vinyl lactams or vinyl ammonium compounds as additional monomer building blocks. Examples of suitable copolymers or terpolymers are octylacrylamide/acrylic acid/butylaminoethyl methacrylic acid terpolymer (CTFA: Octylacrylamide/Acrylates/Butylaminoethyl Methacrylate Copolymer), e.g., Amphomer®, National Starch (U.S.A.); acrylic acid/acrylamide copolymer (CTFA: Acrylates/Acrylamide Copolymer), e.g., Ultrahold 8®, BASF (Germany); vinyl acetate/crotonic acid copolymer (CTFA: VA/Crotonates Copolymer), e.g., Luviset CA 66®, BASF, or Resyn 28-1310®, National Starch (U.S.A.); acrylic acid/polyvinylpyrrolidone copolymer (CTFA: Acrylates/PVP Copolymer), e.g., Luviflex VBM 35®, BASF; methyl vinyl ether/maleic anhydride copolymer (CTFA: PVM/MA Copolymer), e.g., Gantrez®, GAF (U.S.A.), or vinyl acetate/crotonic acid/vinyl neodecanoate copolymer (CTFA: VA/Crotonates/Vinyl Neodecanoate Copolymer), e.g., Resyn 28-2930, National Starch (U.S.A.).

The names of the polymers mentioned by way of example were taken from the CTFA Cosmetic Ingredient Dictionary, 4th edition, 1991.

The aqueous composition according to the invention preferably contains 55 to 96 percent by weight water (component (C)).

The pH of the composition is in the range of 1.5 to 11.5, preferably 3.5 to 8.5. The pH can be adjusted by means of physiologically tolerated acids or bases, e.g., lactic acid, citric acid, glyoxylic acid, formic acid, acetic acid, phosphoric acid, aminomethyl propanol, triisopropylamine, sodium hydroxide, potassium hydroxide, ammonia or monoethanolamine.

Further, the composition according to the invention can contain cosmetic additives conventionally used in hair treatment compositions, e.g., anionic, amphoteric or nonionic surfactants, i.e. wetting agents and emulsifiers, such as ethoxylated fatty alcohols, fatty acid alkanolamides, alkylbetaines, alkylaminobetaines,. alkylsulfobetaines and fatty acid alkylamidobetaines in quantities of 0.01 to 20 percent by weight; foam synergists, foam stabilizers, sequestering agents, emulsifiers, natural ingredients, pigments, perfume oils in quantities of 0.1 to 5.0 percent by weight, opacifiers such as ethylene glycol distearate in quantities of approximately 0.5 to 5.0 percent by weight, pearlescing agents such as a mixture of fatty acid monoalkylolamide and ethylene glycol distearate in quantities of approximately 1.0 to 10.0 percent by weight, buffers such as sodium citrate or sodium phosphate in quantities of 0.1 to 1.0 percent by weight, dyes such as fluorescein sodium salt, Yellow ZN3 (C.I. 47,055) in quantities of 0.1 to 1.0 percent by weight, hair grooming additions such as fatty acid esters, fatty alcohols, fatty acid glycerides, ethoxylated or propoxylated saturated fatty alcohols, conditioners such as lanolin derivatives, cholesterol and pantothenic acid in quantities of 0.1 to 1.0 percent by weight, as well as physiologically tolerated inorganic salts such as sodium chloride and sodium sulfate, also moistening agents, lightfastness agents, antioxidants, complexing agents, ingredients for preventing dandruff, cosmetic oils, waxes and preservatives.

The typical cosmetic ingredients for hair treatment compositions can be contained in quantities of 0.1 to 20 percent by weight.

The hair treatment composition according to the invention can take the form of a hair conditioner, shampoo or hair setting or fixing composition. If desired, it can also be used to dye or tint hair at the same time when it contains dyestuffs which are directly absorbed in the hair. These preparations are known commercially, for example, as dye fixing compositions or tint fixing compositions. They contain, in addition, conventional dyes which are absorbed directly in the hair, e.g. aromatic nitro dyes such as 1,4-diamino-2-nitrobenzene, picramic acid, 1-hydroxy-2-amino-4-nitrobenzene and 1,4-bis-(2-hydroxyethyl)-amino-2-nitro-5-chlorobenzene, azo dyes such as Acid Brown 4 (C.I. 14,805), anthraquinone dyes such as Disperse Violet 4 (C.I. 61,105) and triphenylmethane dyes such as Basic Violet I (C.I. 42,535), Basic Violet 14 (C.I. 42,510) or Basic Blue 7 (C.1.42,595:1). Depending on their substituents, these dyes can have an acidic, nonionic or alkaline character. The total concentration of such dyes in the composition according to the invention is generally approximately 0.01 to 2.0 percent by weight.

The hair treatment composition according to the invention can take the form of a lotion, a spray lotion, a gel or a cream.

The composition according to the invention can also be placed in a container under pressure together with a propellant and dispensed from this container in the form of an aerosol spray or aerosol foam. It can also take the form of a non-aerosol hair spray or non-aerosol foam which can be sprayed by a suitable mechanically operated spraying device.

By mechanically operated spraying device is meant devices which spray liquids without the use of liquified propellants. For example, a suitable mechanical spray device can be a spray pump or a flexible container which is provided with a spray valve and contains the aforementioned cosmetic composition under pressure. This flexible container expands and the composition can be dispensed in a continuous manner from this container due to the contraction of the flexible container by opening the spray valve.

When the composition according to the invention takes the form of an aerosol hair spray or aerosol foam, it contains, in addition, 2 to 98 percent by weight of propellant and is introduced into a container under pressure. Some examples of suitable propellants are highly volatile hydrofluorochlorocarbons, such as difluorochloromethane or trichloromonofluoromethane, tetrafluorodichloroethane or lower alkanes, such as n-butane, i-butane and propane, or dimethyl ether and other gaseous propellants, e.g. $N_2$, $N_2O$ and $CO_2$, at the appropriate pressures, as well as mixtures of the aforementioned compounds. Of the propellants mentioned above, lower alkanes and mixtures of lower alkanes are preferred.

The composition can be produced by current conventional mixing and stirring apparatuses. In the first step, the film-forming or fixing polymer or polymer mixture is dissolved in water. All additional components, with the exception of the thickener, are then added. Finally, the thickener is added and, when appropriate, the composition is adjusted to the pH required for the precipitation of the film-forming polymer or polymer mixture.

The composition according to the invention does not burden hair and is therefore particularly suitable for fine hair.

Particularly, when used as a hair fixing composition, it achieves outstanding hold of hairstyles without making hair sticky or loading it with a high proportion of fixing polymers. Fine hair is given body and volume. As a hair setting gel, the composition for treating hair shows improved fixing characteristics compared with conventional gels. The composition does not contain organic solvents and therefore has a less harmful impact on people and on the environment.

The following examples explain the subject matter of the invention in more detail.

EXAMPLES

Example 1
Setting lotion

| | |
|---|---|
| 1.00 g | methyl vinyl ether/maleic anhydride copolymer crosslinked with decadiene (Stabileze 06R, ISP, England) |
| 3.50 g | octylacrylamide/acrylic acid/butylaminoethyl methacrylate copolymer (AmphomerR, National Starch, U.S.A.) |
| 2.18 g | aminomethyl propanol |
| 0.20 g | hydrogenated castor oil ethoxylated with 40 moles ethylene oxide |
| 0.20 g | p-hydroxybenzoic acid methyl ester |
| 0.20 g | perfume oil |
| 92.72 g | water |
| 100.00 g | |

The setting lotion has a pH of 6.5. The viscosity of the composition is 110 mPa.s as measured by a Haake viscometer at 30° C., rod 11, with a support weight of 10 g.

Example 2
Cream Gel for Normal Fixing

| | |
|---|---|
| 6.96 g | corn starch |
| 1.70 g | vinyl acetate/crotonic acid copolymer (Luviset CA 66R, BASF, Germany) |
| 0.15 g | potassium hydroxide |
| 0.30 g | hydrogenated castor oil ethoxylated with 40 moles ethylene oxide |
| 0.20 g | p-hydroxybenzoic acid methyl ester |
| 0.15 g | perfume oil |
| 90.54 g | water |
| 100.00 g | |

The pH of the composition is adjusted to 6.5 with citric acid.

Example 3
Foam Fixing Composition for Normal Fixing

| | |
|---|---|
| 1.2 g | hydroxyethyl cellulose |
| 1.7 g | vinyl acetate/crotonic acid copolymer (Resyn 28-1310R, National Starch, U.S.A.) |
| 0.3 g | aminomethyl propanol |
| 0.2 g | hydrogenated castor oil ethoxylated with 40 moles ethylene oxide |
| 0.2 g | p-hydroxybenzoic acid methyl ester |
| 0.1 g | perfume oil |
| 96.3 g | water |
| 100.00 g | |

The pH of the composition is adjusted to 6.5 with citric acid. The composition is then introduced into a compressed-gas container with a propane/butane propellant mixture (1.5 bar) in a weight ratio of 95:5 (composition: propellant).

Example 4
Hair Conditioning Foam

| | |
|---|---|
| 1.0 g | acrylic acid homopolymer |
| 1.8 g | acrylic acid/ethyl acrylate/N-tert.-butylacrylamide copolymer (Ultrahold 8R, BASF, Germany) |
| 0.8 g | aminomethyl propanol |
| 0.3 g | castor oil ethoxylated with 35 moles ethylene oxide |
| 0.4 g | vinylpyrrolidone/dimethylaminomethacrylate copolymer (Gafquat 755 NR, GAF, U.S.A.) |
| 0.3 g | p-hydroxybenzoic acid methyl ester |
| 0.2 g | perfume oil |
| 95.2 g | water |
| 100.0 g | |

The pH of the composition is adjusted to 6.5 with citric acid. The composition is then introduced into a compressed-gas container with a propane/butane propellant mixture (1.5 bar) in a weight ratio of 95:5 (composition: propellant).

Example 5
Cream Gel for Intensive Fixing

| | |
|---|---|
| 6.96 g | corn starch |
| 3.50 g | vinyl acetate/crotonic acid copolymer (Luviset CA 66R, BASF, Germany) |
| 0.30 g | potassium hydroxide |
| 0.30 g | hydrogenated castor oil ethoxylated with 40 moles ethylene oxide |
| 0.20 g | p-hydroxybenzoic acid methyl ester |
| 0.20 g | perfume oil |
| 88.54 g | water |
| 100.00 g | |

The pH of the composition is adjusted to 6.5 with citric acid.

Example 6
Gel-Spray

| | |
|---|---|
| 1.20 g | hydroxyethyl cellulose |
| 1.50 g | vinyl acetate/crotonic acid copolymer (Resyn 28-1310R, National Starch, U.S.A.) |
| 0.24 g | aminomethyl propanol |
| 0.30 g | hydrogenated castor oil ethoxylated with 35 moles ethylene oxide |
| 0.30 g | p-hydroxybenzoic acid methyl ester |
| 0.20 g | perfume oil |
| 96.26 g | water |
| 100.00 g | |

The pH of the composition is adjusted to 6.3 with citric acid. The composition is introduced as a non-aerosol pump spray.

Example 7
Liquid Cream-Gel for Gentle Fixing

| | |
|---|---|
| 0.20 g | acrylic acid homopolymer |
| 0.20 g | vinyl acetate/crotonic acid copolymer (Resyn 28-1310R, National Starch, U.S.A.) |
| 0.12 g | aminomethyl propanol |
| 0.20 g | hydrogenated castor oil ethoxylated with 40 moles ethylene oxide |
| 0.20 g | p-hydroxybenzoic acid methyl ester |

-continued

| | |
|---|---|
| 0.10 g | perfume oil |
| 98.98 g | water |
| 100.00 g | |

The composition has a pH of 6.6.

Example 8
Hair Fixing Composition

| | |
|---|---|
| 12.5 g | hydroxypropylcellulose |
| 0.5 g | acrylic acid homopolymer |
| 8.0 g | vinyl acetate/crotonic acid copolymer (Resyn 28-1310$^R$, National Starch, U.S.A.) |
| 1.0 g | aminomethyl propanol |
| 0.2 g | nonylphenol ethoxylated with 14 moles ethylene oxide |
| 0.2 g | p-hydroxybenzoic acid methyl ester |
| 0.1 g | perfume oil |
| 77.5 g | water |
| 100.00 g | |

The composition has a pH of 6.5.

Example 9
Fixing Tonic

| | |
|---|---|
| 0.5 g | acrylic acid homopolymer |
| 2.6 g | vinyl acetate/crotonic acid copolymer (Resyn 28-1310$^R$, National Starch, U.S.A.) |
| 0.3 g | aminomethyl propanol |
| 2.2 g | cetyl/stearyl alcohol (1:1) |
| 0.4 g | sodium cetyl/stearyl sulfate |
| 0.8 g | lauryl alcohol ethoxylated with 2 moles ethylene oxide |
| 2.1 g | petrolatum |
| 0.4 g | p-hydroxybenzoic acid methyl ester |
| 0.2 g | perfume oil |
| 90.5 g | water |
| 100.00 g | |

The composition has a pH of 6.5.

Example 10
Fixing Shampoo

| | |
|---|---|
| 1.2 g | acrylic acid homopolymer |
| 3.0 g | vinyl acetate/crotonic acid copolymer (Resyn 28-1310$^R$, National Starch, U.S.A.) |
| 1.5 g | aminomethyl propanol |
| 35.0 g | lauryl ether sulfate (28-percent aqueous solution) |
| 10.0 g | cocoamidopropyl betaine |
| 0.2 g | perfume oil |
| 49.1 g | water |
| 100.00 g | |

The composition has a pH of 6.4.

Example 11
Tinting Fixing Composition

| | |
|---|---|
| 0.20 g | methyl vinyl ether/maleic anhydride copolymer crosslinked with decadiene (Stabilize 06$^R$, ISP, USA) |
| 2.20 g | vinyl acetate/crotonic acid copolymer (Luviset CA 66$^R$, BASF, Germany) |
| 0.19 g | potassium hydroxide |
| 0.20 g | castor oil ethoxylated with 35 moles ethylene oxide |
| 0.20 g | p-hydroxybenzoic acid methyl ester |
| 0.05 g | Acid Brown 4 (C. I. 41,805) |
| 0.20 g | perfume oil |
| 96.76 g | water |
| 100.00 g | |

The composition has a pH of 6.3.

Example 12
Comparison Experiments

Comparison experiments were performed in which the curl retention for fixing compositions according to the invention and fixing compositions according to the prior art described in published European Patent Application EP 0 034 190 A1 was measured.

Six compositions were prepared having the compositions described hereinbelow. Compositions A1, B1 and C1 were compositions containing undissolved polymer according to the invention. Compositions A2, B2 and C2 were compositions containing an undissolved complex of anionic polymer and cationic surfactant according to EP 0 034 190 A1.

a) Tested Compositions

| a) Tested Compositions | | |
|---|---|---|
| Ingredient | Composition | |
| | A1 | A2 |
| Methylvinylether/maleic acid monobutylester copolymer | 0.15 g | 0.15 g |
| 2-amino-2-methyl-1-propanol | 0.05 g | 0.05 g |
| cetyltrimethyl ammonium chloride | — | 0.30 g |
| hydroxyethyl cellulose | 0.75 g | 0.75 g |
| citric acid | 0.21 g | |
| water | 98.84 g | 98.75 g |
| | 100.00 g | 100.00 g |
| pH | 4.0 | 6.1 |
| | B1 | B2 |
| Methylvinylether/maleic acid monoethylester copolymer | 0.40 g | 0.40 g |
| sodium hydroxide | 0.08 g | 0.08 g |
| oleyldimethylbenzyl ammonium chloride | — | 0.80 g |
| hydroxyethyl cellulose | 1.40 g | 1.40 g |
| citric acid | 0.75 g | — |
| water | 97.37 g | 97.37 g |
| | 100.00 g | 100.00 g |
| pH | 3.7 | 7.3 |
| | C1 | C2 |
| Methylvinylether/maleic acid monobutylester copolymer | 0.40 g | 0.40 g |
| sodium hydroxide | 0.07 g | 0.07 g |
| oleyldimethylbenzyl ammonium chloride | — | 0.80 g |
| hydroxyethyl cellulose | 1.40 g | 1.40 g |
| citric acid | 0.58 g | — |
| water | 97.55 g | 97.33 g |
| | 100.00 g | 100.00 g |
| pH | 3.9 | 6.8 | b) Experimental Methods and Measurement Conditions

Standardized hair strands with 100 hairs were cut to a length of 7.5 cm, tied together at their ends and weighed to ensure that they had an equal weight of about 0.05 g. The strands are placed individually in plastic bags, wetted with water and each strand was treated with 60 microliters of one of the above tested compositions for 10 minutes in the closed bags. The hair strands were applied to a curler and dried at 70° C. for ten minutes. The curlers with the hair strands were further dried for 60 minutes in a desiccator filled with calcium chloride. The curled hair strands were removed from the curlers and the curl retention was measured by measuring the length of each curl before and after hanging in a conditioned room for 5 hours at 20° C. and 65 % relative humidity.

c) Results

The curl retention results are shown in the following Table:

TABLE I

Curl Retention for Hair Strands Treated with the Tested Compositions

| Simple | A1 | A2 | B1 | B2 | C1 | C2 |
|---|---|---|---|---|---|---|
| % Curl Retention | 65.6 | 62.5 | 68.6 | 64.2 | 70.7 | 66.0 |

The samples A1, B1 and C2 according to the invention are turbid heterogeneous dispersions at their respective pH-values of 4.0, 3.7 and 3.9 but clear homogeneous solutions at the pH values of the corresponding comparison sample. The comparison samples A2, B2 and C2 are turbid heterogeneous dispersion at their respective pH-values of 6.1, 7.3 and 6.8.

The curl retention measurements show an increase in curl retention for the samples according to the invention as compared to the respective comparison samples, although the samples according to the invention are of a simplified composition.

While the invention has been illustrated and described as embodied in an aqueous hair treatment composition containing a thickener and a fixing water-soluble polymer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by letters patent is set forth in the appended claims.

We claim:

1. An aqueous hair fixing composition for fixing hair comprising:

0.1 to 30 percent by weight of at least one thickener selected from the group consisting of polymers of acrylic acid, polymers of methacrylic acid, polymers of crotonic acid, polymers of acrylic acid esters, polymers of methacrylic acid esters, polymers of crotonic acid esters, polymers of acrylic acid salts, polymers of methacrylic acid salts, polymers of crotonic acid salts, acrylamide/acrylate copolymers, copolymers of acrylic acid and an ester of methacrylic acid and stearyl alcohol ethoxylated with 20 Mol of ethylene oxide, diene-crosslinked-unsaturated acid anhydride/alkyl vinyl ether copolymers, polyethylene glycols, polypropylene glycols, polyethylene glycol/polypropylene glycol copolymers, polysaccharides, hydrolyzates of polysaccharides, gelatin, hectorite and bentonite;

0.1 to 25 percent by weight of at least one film-forming polymer selected from the group consisting of vinyl acetate/crotonic acid copolymer, acrylic acid/acrylamide copolymer and methyl vinyl ether/maleic anhydride copolymer; and 45 to 99.8 percent by weight water;

and containing no organic solvents, no cationic surfactants and no cationic polymers and having a pH at which said at least one film-forming polymer is at least partially precipitated.

2. The aqueous hair fixing composition as defined in claim 1, wherein said at least one thickener is present in an amount of 0.15 to 15 percent by weight.

3. The aqueous hair fixing composition as defined in claim 1, containing 0.2 to 10 percent by weight of said at least one film-forming polymer.

4. The aqueous hair fixing composition as defined in claim 1, containing 55 to 96 percent by weight of said water.

5. The aqueous hair fixing composition as defined in claim 1, wherein said polysaccharides are selected from the group consisting of cellulose, hydroxypropyl cellulose, starch, chitin, chitosan, alginic acid, alginates, carrageenan, maltodextrin, dextrin, guar gum, xanthan gum, gellan gum and hyaluronic acid, and said at least one thickener is selected from the group consisting of said polysaccharides, said gelatin, said hectorite and said bentonite.

6. The aqueous hair fixing composition as defined in claim 1, wherein said at least one film-forming polymer is soluble in said water in a salt form thereof and is insoluble in said water in one of a free base form and a free acid form.

7. The aqueous hair fixing composition as defined in claim 1, further comprising from 0.01 to 20 percent by weight of at least one surfactant member selected from the group consisting of anionic, amphoteric and nonionic surfactants.

8. The aqueous hair fixing composition as defined in claim 1, further comprising an amount of a physiologically tolerated acid or base sufficient to provide said pH at which said at least one film-forming polymer is at least partially precipitated.

9. The aqueous hair fixing composition as defined in claim 8, wherein said physiologically tolerated acid is selected from the group consisting of lactic acid, citric acid, glyoxylic acid, formic acid, acetic acid and phosphoric acid and said physiologically tolerated base is selected from the group consisting of aminomethyl propanol, triisopropylamine, sodium hydroxide, potassium hydroxide, ammonia and monoethanolamine.

10. The aqueous hair fixing composition as defined in claim 1, further comprising from 0.1 to 5.0 percent by weight perfume oil.

* * * * *